(12) United States Patent
Chen et al.

(10) Patent No.: US 11,001,560 B2
(45) Date of Patent: May 11, 2021

(54) COMPOUND FOR BLOCKING ABSORPTION OF HEAVY METALS BY PLANTS AND A COMPOSITION CONTAINING THE SAME

(71) Applicant: SICHUAN HUI TAI AGRICULTURAL TECHNOLOGY CO. LTD., Chengdu (CN)

(72) Inventors: Lezhang Chen, Chengdu (CN); Junbo Yang, Chengdu (CN)

(73) Assignee: SICHUAN HUI TAI AGRICULTURAL TECHNOLOGY CO. LTD., Chengdu (CN)

( * ) Notice: Subject to any disclaimer, the term of this patent is extended or adjusted under 35 U.S.C. 154(b) by 0 days.

(21) Appl. No.: 16/699,517

(22) Filed: Nov. 29, 2019

(65) Prior Publication Data

US 2020/0172490 A1    Jun. 4, 2020

(30) Foreign Application Priority Data

Nov. 30, 2018  (CN) .......................... 201811448494.4

(51) Int. Cl.
  *C07D 225/06*  (2006.01)
  *A01N 43/34*   (2006.01)
  *A01N 65/08*   (2009.01)

(52) U.S. Cl.
  CPC ........... *C07D 225/06* (2013.01); *A01N 43/34* (2013.01); *A01N 65/08* (2013.01)

(58) Field of Classification Search
  CPC .................................................. C07D 225/06
  See application file for complete search history.

*Primary Examiner* — Heidi Reese
(74) *Attorney, Agent, or Firm* — SZDC Law P.C.

(57) ABSTRACT

The invention relates to a compound capable of blocking the absorption of heavy metals by plants and a composition containing the same. The compound was extracted from *Aegiceras corniculatum*. The compound is extracted by enzyme extraction, filtration, concentrating and drying. The compound is derived from natural plants, and no organic solvents are used in the extraction process. The compound and the composition formed by the compound have a certain barrier effect on the absorption of heavy metals by plants.

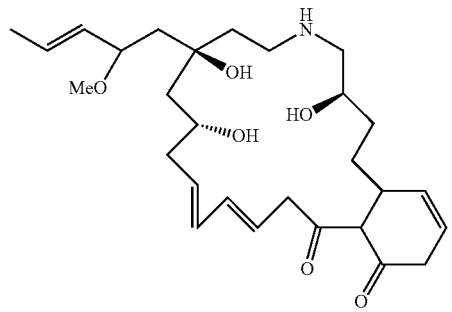

5 Claims, No Drawings

COMPOUND FOR BLOCKING ABSORPTION OF HEAVY METALS BY PLANTS AND A COMPOSITION CONTAINING THE SAME

This application claims priority to Chinese Patent Application No.: 201811448494.4, filed on Nov. 30, 2018, which is incorporated by reference for all purposes as if fully set forth herein.

FIELD OF THE INVENTION

The present invention relates to the field of agricultural environment ecology, in particular, to a method for preventing and controlling heavy metal pollution in farmland soil. The invention uses natural plants to prevent and control heavy metal pollution in farmland, realizes the combination of environmental protection and heavy metal pollution prevention, effectively reduces the absorption and accumulation of heavy metals by crops, and meets the safety and health standards for agricultural products.

BACKGROUND OF THE INVENTION

When plants are poisoned by cadmium, generally, the growth and development of cells and the entire plant are strongly inhibited, and mitochondria and chloroplasts are greatly damaged, resulting in affected respiration and photosynthesis. Leaves turn yellow, plant biomass declines, and dry mass reduces. Water and ion migration in guard cells are greatly affected, resulting in water shortage and wilting of the entire plant. At the same time, plant cell membrane permeability increases and free proline accumulation in the body increases, which in severe cases leads to plant death. Cadmium mainly affects the physiological metabolism of plants. Cadmium also inhibits cell division and plant growth. Experiments have shown that the effect of cadmium on the auxin carrier is related to the inhibition of cell elongation. When Donghua Liu and other researchers studied the effect of cadmium on the division and growth of onion root tip cells, they found that it inhibited cell division by affecting calmodulin involved in the assembly and disassembly of spindle tubulin. After plants absorb heavy metal cadmium, chlorophyll synthesis in the body is inhibited, which ultimately leads to the inhibition of photosynthesis. Treatment of rice plants at the tillering stage with cadmium revealed that the chlorophyll content in rice leaves was significantly reduced and chlorophyll a was reduced less than chlorophyll b. This shows that heavy metal cadmium has a significant effect on the pigment of rice leaves at the tillering stage. Cadmium can impair plant tolerance to water stress. When the relative water content and the leaf water content are relatively high, the elasticity of the plant cell wall becomes poor, causing the loss of turgor pressure, which causes the plant's tolerance to water stress to decrease. When plants are treated with cadmium, the stomata resistance of the plant leaves will increase, which causes the stomata pore size of the plant leaves to decrease, and the rate of transpiration slows down, which weakens the main motive force of the plant for water absorption and transportation. In addition, cadmium can also cause the xylem cell wall to degenerate, reducing the transport of water to the xylem at the same time, and eventually leading to plant wilting. Mitochondria are more sensitive organelles when poisoned by cadmium. When amaranth is poisoned by heavy metal cadmium, the mitochondria of leaf mesophyll cells disintegrates first, and the nucleoli divides into many pieces. Cadmium ions can increase the passive permeability of mitochondrial hydrogen ions and prevent oxidative phosphorylation of mitochondria. They can also increase the resistance of plant stomata, which directly affects the migration of water and ions in guard cells and hinders plant respiration. Peng Ming et al. observed the disintegration or swelling of plastid matrix particles when studying the damage of cadmium ions to maize seedlings. In order to reduce the use of heavy metals in plants, the following methods are generally available:

The bioavailability of heavy metals in soil depends on whether the heavy metals are easily absorbed by plants. Bioavailability is largely determined by plant rhizosphere microorganisms. Rhizosphere microorganisms can change the solubility, mobility, availability and specificity of metals by changing the pH value. The presence of rhizobia (a soil-fungi strain that is mutually beneficial with the roots of most plant ducts) can promote detoxification of plants and increase their tolerance to heavy metals. *P. aeruginosa* reduces the absorption of $Cd^{2+}$ by pumpkin and mustard by increasing the utilization of $Cd^{2+}$ in the soil. In order to prevent Cd from flowing into their host, $Cd^{2+}$ will also be bound to sulfur-rich compounds such as glutathione and γ-glutamylcysteine to reduce the utilization of cadmium in plants.

The cell wall is the first structure where plants are exposed to heavy metals and contains xanthones and fructooligosaccharides. Thrombin exists in a large number of root endothelial cell walls, which can act as a barrier to control the cell body's absorption of water and minerals, and affect the accumulation and transport of nutrients and minerals. Fructooligosaccharides contain polysaccharides and are capable of binding divalent and trivalent heavy metal ions. Most essential and non-essential elements enter the plant in the form of divalent ions, such as $Zn^{2+}$, $Cd^{2+}$, $Fe^{2+}$, $Mn^{2+}$, and $Cu^{2+}$. Therefore, the plant body can promote the binding of heavy metal cations to the cell wall by changing the composition of the cell wall, which can reduce its own absorption of toxic metals. Under cadmium stress, it was found that the number of lignin biosynthesis genes and cell enlargement genes in *Arabidopsis thaliana* were increased, but high levels of expression were maintained in thlaspi. It can be known that plants sensitive to $Cd^2+$, such as *Arabidopsis thaliana*, can use lignin as a physical barrier to prevent $Cd^{2+}$ from entering the plant.

Metal precipitation is another way to limit heavy metals to enter the plant body. Just as in *Arabidopsis thaliana*, a plant that accumulates heavy metals at excessive levels, cadmium phosphate compounds accumulate more outside the cell wall of the root epidermis. It shows that the potential root cell wall structure can reduce the bioavailability of heavy metals in plants, thereby enhancing the plant's tolerance to heavy metals.

There are several ways for heavy metals to enter plant symbiotic bodies: simple diffusion, passive transport of channel proteins, or active transport of transport proteins. Among them, active transporter plays a major role. This type of transporter is generally called a metal transporter, which has different transport capabilities for different heavy metals. $Cd^{2+}$ is chemically similar to Zn and Fe. At present, no specific transporter of cadmium has been reported in plant cells. The absorption of cadmium in plants is likely to be carried out by ZIP transporter. This transporter has a strong specific transport capacity for $Zn^{2+}$ or $Fe^{2+}$, but it has a poor transport capacity for cadmium. Therefore, there is a chance of $Cd^{2+}$ absorption in root cells. The super-absorption of cadmium by thlaspi eventually accumulated into the xylem juice. Under iron deficiency, the IRT1 gene can be strongly induced, causing a strong uptake of cadmium in plants. However, this view has not yet been confirmed.

Heavy metals generally need to be chelated by ligands through the cell membrane to reduce unnecessary association with cell complexes. These ligands include oligopeptides, organic acids, amino acids, and proteins. The heavy metal-ligand complex structure is an important part of the molecular mechanism of heavy metal balance, and metal chelation products play an important role in the plant's resistance to heavy metal stress. Compared with heavy metal non-super-accumulation species, heavy metal hyper-accumulation species have higher phytochelatin accumulation, which indicates that plant chelate peptides play an important role in detoxification of heavy metals, isolation of heavy metals, and elimination of heavy metals.

The present application discovered a compound having an ability to absorb heavy metals by extracting the plants that have a good absorption effect on heavy metal.

*Aegiceras corniculatum* is one of the important tree species that make up the mangrove forest. It is produced in the southern coast of China. The seed germinates before it leaves the mother tree, so it is called viviparous tree. Shrubs or small trees; leaf leathery, obovate, blunt; flowers bisexual, 5 petals, stipitate, arranged in gum or terminal umbels; sepals shingled; corolla tube short, 5 lobes; 5 stamens; filaments basal connate, born at the base of the corolla, with a diaphragm in the medicine room, divided into several chambers; upper ovary, oblong, with many ovules; capsules cylindrical, sharp, curved like horns, leathery. *Aegiceras corniculatum*, a common mangrove species, grows at the end of the offshore side. The leaf pattern is clearer than that of Kandelia, the petiole is red, and salt is often excreted on the leaf surface. The roots of the *Aegiceras corniculatum* are stretched horizontally under the soil surface to stabilize the tree body. The flowering period is from January to April and the fruit period is from May to September. *Aegiceras corniculatum* is also a common tree species in Fujian Province and has low temperature resistance. *Aegiceras corniculatum* is be widely distributed, but not as cold-resistant as Kandelia. It is widely distributed in Guangdong Province, Guangxi Province, and Fujian Province, especially at the outer edge of tidal flats or at the intersection of estuaries and the outer edge of Kandelia forest. The wood of *Aegiceras corniculatum* is yellow-green in appearance. The bases of the trees are more branched and the tops of the trees are flat. The height of this species decreases with increasing latitude. The structure of *Aegiceras corniculatum* forest is simple and has only one layer. Due to the many branches at the base, the diameter of the base is generally about 15 cm, and the larger one can reach 30 cm. Large plant clumps can produce short and dense pillar roots to support the tree body. Occasionally, small trees, such as red mangrove and bony soil, are also grown in the *Aegiceras corniculatum* forest, and they may grow in layers with candel.

It is known that plants of the same type can have different absorption and enrichment abilities of different heavy metal elements, and different types of plants can also have different absorption and enrichment abilities of the same heavy metal element. *Aegiceras corniculatum* has a certain absorption effect on heavy metals, and different parts have different absorption capacities for heavy metals. The absorption capacity of the same heavy metal element in different parts of *Aegiceras corniculatum* is root>stem>leaf>branch. Plants absorb too much heavy metals, which can seriously affect plant growth and development, and even cause genetic variation. At present, the way to prevent plants from absorbing heavy metals is often to add additional chemicals. While these chemicals absorb heavy metals, they also cause secondary pollution to the soil and plants. Based on this, the applicant's goal is to develop a component that blocks heavy metals, and at the same time isolates and absorbs heavy metals, while achieving the purpose of environmental protection.

SUMMARY OF THE INVENTION

Therefore, the object of the present invention is to disclose an *Aegiceras corniculatum* extract;

Another object of the present invention is to disclose a method for preparing an *Aegiceras corniculatum* extract;

Another object of the present invention is to disclose the use of *Aegiceras corniculatum* extract for isolating plants from absorbing heavy metals;

Another object of the present invention is to disclose a composition containing the extract of the present invention.

The object of the present invention is achieved by the following methods.

The inventors have conducted research on different medicinal parts of *Aegiceras corniculatum*, and carried out extraction and activity research on the whole tree, roots, stems, leaves and branches of *Aegiceras corniculatum*. There is a difference in the activities of stem, leaf, and branch in absorbing heavy metals. The order of the absorption activity is root>stem>leaf>branch. The present inventor learned from this discovery, and selected the below ground part of the *Aegiceras corniculatum* for extraction.

The purpose of the invention is achieved by the following technical solutions:

A compound represented by the following formula I:

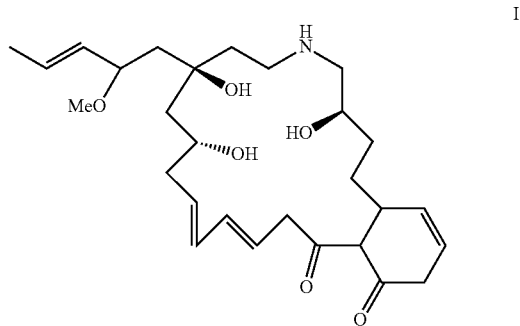 [SMILES: C/C=C/C(C[C@]1(O)CCNC[C@H](O)CCC2C=CCC(=O)C2C(=O)C/C=C/C=C/C[C@@H](O)C1)OC]

It was prepared by the following method: fresh or dried *Aegiceras corniculatum* is mixed with water for enzymatic extraction, and the extract is filtered and concentrated to a relative density of 1.05 to 1.1 g/mL at 80-85° C., and dried.

Preferably, the above ground or below ground part of *Aegiceras corniculatum* were used. The above-ground parts were preferably from leaves, flowers, stems or seeds; and the below ground parts were preferably the roots.

The compound of formula I was prepared by the following method, and the method included the following steps:

(1) drying and pulverizing *Aegiceras corniculatum* raw materials and sieving;

(2) mixing the material in step (1) with water at a weight ratio of 1:10~1:15, adding 0.2 wt %-0.3 wt % of a biological enzyme based on the weight of the raw material, adjusting the pH to 2-10, and stirring at a constant temperature of 35-40° C. for 2-3 h;

(3) after the completion of the extraction, boiling the extract in step (2) for 5-10 minutes and cooling;

(4) concentrating the filtered extract of step (3) to a relative density of 1.05 to 1.1 g/mL at 80 to 85° C., and drying;

(5) recrystallizing the extract of step (4) with V ethanol: V petroleum ether=3:1 to obtain a light yellow flaky crystal, i.e., the compound of formula I.

The preparation method of the compound includes the following steps:

(1) drying and pulverizing *Aegiceras corniculatum* raw materials and sieving;

(2) mixing the material in step (1) with water at a weight ratio of 1:10~1:15, adding 0.2 wt %-0.3 wt % of a biological enzyme based on the weight of the raw material, adjusting the pH to 2-10, and stirring at a constant temperature of 35-40° C. for 2-3 h;

(3) after the completion of the extraction, boiling the extract in step (2) for 5-10 minutes and cooling;

(4) concentrating the filtered extract of step (3) to a relative density of 1.05 to 1.1 g/mL at 80 to 85° C., and drying;

(5) recrystallizing the extract of step (4) with V ethanol: V petroleum ether=3:1 to obtain a light yellow flaky crystal, i.e., the compound of formula I.

Preferably, the biological enzyme used for the enzymatic hydrolysis of the organism is pectinase (enzymatic activity ≥10,000 u/g), cellulase (enzymatic activity ≥10,000 u/g), neutral protease (enzymatic activity ≥300,000 u/g), or papain (enzyme activity ≥400,000 u/g);

Preferably, the drying method is vacuum drying or spray drying.

A composition comprising a compound of formula I above, and an agriculturally acceptable auxiliary agent.

The compound and composition can be used in the field of agriculture, preferably, be used to block plants from absorbing heavy metals, and the plants are preferably food crops.

DETAILED DESCRIPTION OF THE ILLUSTRATED EMBODIMENTS

The present invention is further described below through examples. It should be understood that the methods described in the embodiments of the present invention are only used to illustrate the present invention, rather than limiting the present invention. Simple improvements to the preparation method of the present invention are within the scope of protection of the present invention. All raw materials and solvents used in the examples are commercially available products.

The *Aegiceras corniculatum* extract of the present invention was obtained by the following method:

(1) drying and pulverizing *Aegiceras corniculatum* raw materials and sieving;

(2) mixing the material in step (1) with water at a weight ratio of 1:10~1:15, adding 0.2 wt %-0.3 wt % of a biological enzyme based on the weight of the raw material, adjusting the pH to 2-10, and stirring at a constant temperature of 35-40° C. for 2-3 h;

(3) after the completion of the extraction, boiling the extract in step (2) for 5-10 minutes and cooling;

(4) concentrating the filtered extract of step (3) to a relative density of 1.05 to 1.1 g/mL at 80 to 85° C., and drying;

(5) recrystallizing the extract of step (4) with V ethanol: V petroleum ether=3:1 to obtain a light yellow flaky crystal, i.e., the compound of formula I.

Preferably, the biological enzyme used for the enzymatic hydrolysis of the organism is pectinase (enzymatic activity ≥10,000 u/g), cellulase (enzymatic activity ≥10,000 u/g), neutral protease (enzymatic activity ≥300,000 u/g), or papain (enzyme activity ≥400,000 u/g);

Preferably, the drying method is vacuum drying or spray drying.

EXAMPLE 1

Pectinase (Enzyme Activity ≥10,000 u/g) (No.: A-1)

Taking 2 kg of *Aegiceras corniculatum* roots and sieving; adding 20 kg of water and 0.2% biological enzymes, adjusting the pH to 5, stirring at 35° C. for 3 h; boiling for 10 min, cooling; the relative density of the filtrated extract when concentrated to 80° C. was about 1.05 g/mL, drying; recrystallizing with V ethanol: V petroleum ether=3: 1 to obtain 1.5 g of light yellow flaky crystal, i.e., the compound of formula I.

EXAMPLE 2

Neutral Protease (Enzyme Activity ≥300,000 u/g) (No.: A-2)

Taking 5 kg of *Aegiceras corniculatum* roots and sieving; adding 70 kg of water and 0.3% biological enzymes, adjusting the pH to 7, stirring at 40° C. for 3 h; boiling for 10 min, cool; the relative density of the filtrated extract when concentrated to 85° C. was about 1.1 g/mL, drying; recrystallizing with V ethanol: V petroleum ether=3: 1 to obtain 3.2 g of light yellow flaky crystals, i.e., the compound of formula I.

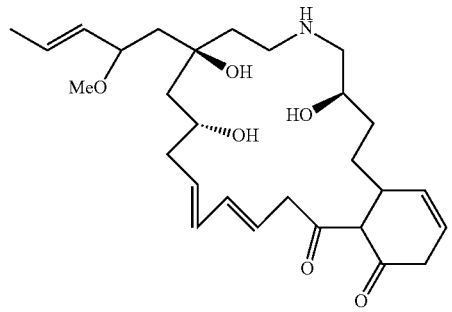 [SMILES: C/C=C/C(C[C@]1(O)CCNC[C@H](O)CCC2C=CCC(=O)C2C(=O)C/C=C/C=C/C[C@@H](O)C1)OC]

Anal. Calcd. For: $C_{28}H_{43}NO_6$, Found: C 68.70; H 8.84; N 2.86; O 19.59.

$^1$HMR (300 MHz, DMSO), δ: 6.17 (s, 1H, H); 6.13 (m, 1H, H); 6.03 (s, 1H, H); 5.85 (m, 1H, H); 5.67 (m, 1H, H); 5.64 (m, 1H, H); 5.63 (m, 1H, H); 5.61 (m, 1H, H); 5.37 (s, 1H, OH); 4.77 (s, 1H, OH); 4.49 (s, 1H, OH); 3.88 (q, 1H, CH); 3.70 (s, 1H, NH); 3.53 (q, 1H, CH); 3.45 (q, 1H, CH); 3.30 (s, 3H, $CH_3$); 3.17 (m, 2H, $CH_2$); 3.15 (m, 1H, CH); 3.14 (m, 2H, $CH_2$); 2.81 (q, 2H, $CH_2$); 2.58 (m, 2H, $CH_2$); 2.52 (m, 1H, CH); 2.21 (m, 2H, $CH_2$); 1.63 (d, 3H, $CH_3$); 1.62 (m, 2H, $CH_2$); 1.61 (m, 2H, $CH_2$); 1.53 (m, 2H, $CH_2$); 1.52 (m, 2H, $CH_2$); 1.38 (m, 2H, CH2).

EXAMPLE 3

Effect of Compound of Formula I on Reducing Heavy Metal Content in Vegetables

Potted experiments were carried out. The test soil was collected from the topsoil (0-20 cm) of farmland in the outskirts of Chengdu, Sichuan Province. The soil type was purple soil, with a total lead content of 1209.21 mg kg$^{-1}$ and a total cadmium content of 8.06 mg kg$^{-1}$. After the soil samples were collected, the plant residues were removed, air-dried, and passed through a 5 mm siever for later use. Test plants were bok choy and pepper. The sieved soil was filled into a tray, and 80 g of soil was filled in each tray. Before the planting, watering was carried out for 3 days to maintain the field water holding capacity of about 60%. Seeds of uniform size were selected. The surface of the seed was sterilized with ethanol: 30% $H_2O_2$ (V:V=1:1) for 3 minutes, and rinsed with sterile deionized water. The sterilized plant seeds were divided into two groups. One group was soaked in a deionized aqueous solution (5 g/L) of the compound of formula I for 4 hours, and was set as the experimental group. The other group was soaked in deionized water for the same time as the control group. The process was repeated 4 times. The seeds after soaking were sowed in a pot. After 1 week after emergence, 3 plants were left in each pot. The above soaking treatment was performed again, and the roots of the experimental group and the control group were soaked with 5 mL of an aqueous solution containing a compound of formula I and deionized water per pot, respectively. Watering the plant daily was necessary to ensure the necessary water for plant growth. Plants were harvested after 40 days of growth. The plants were removed from the pot and washed with deionized water. After harvesting, the plants were cut into roots and above ground parts along the junction of the rhizomes. The plants were put in an oven at 105° C. for 15 minutes, dried at 70° C., and weighed the dry weight of roots and above ground parts. The plant samples were grounded and digested by the nitric acid-perchloric acid method. The contents of heavy metals Pb and Cd in the plants were determined by atomic absorption spectrophotometer. The results are shown in the following table.

|  | Above Ground Parts |  | Below Ground Parts |  |
| --- | --- | --- | --- | --- |
| Samples | Bok Choy | Pepper | Bok Choy | Pepper |
| Cd Concentration in Vegetables (mg/L) | | | | |
| Control Group | 2.71 ± 0.21 | 3.96 ± 0.26 | 5.17 ± 0.18 | 6.25 ± 0.18 |
| Experimental Group | 2.08 ± 0.19 | 2.89 ± 0.39 | 2.01 ± 0.33 | 4.58 ± 0.11 |
| Pb Concentration in Vegetables (mg/L) | | | | |
| Control Group | 3.44 ± 0.13 | 4.17 ± 0.05 | 11.26 ± 1.21 | 9.76 ± 0.21 |
| Experimental Group | 1.51 ± 0.06 | 1.32 ± 0.08 | 6.71 ± 1.08 | 5.11 ± 0.63 |

As can be seen from the table above, compared with the control group, the experimental group can reduce the absorption of heavy metals Cd and Pb by the vegetable above ground parts and the below ground parks. The experimental group was able to significantly reduce the Cd and Pb concentrations in the above ground parts and below ground parts of bok Choy and peppers.

What is claimed is:

1. A method of preparing a compound having the following Formula I comprising:

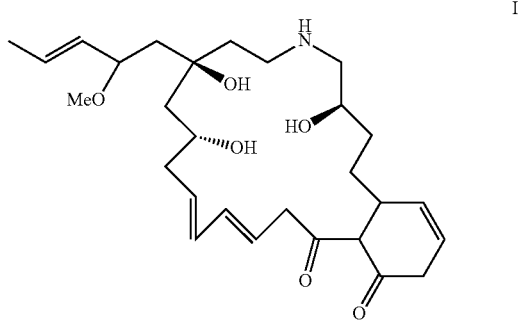 [SMILES: C/C=C/C(C[C@]1(O)CCNC[C@H](O)CCC2C=CCC(=O)C2C(=O)C/C=C/C=C/C[C@@H](O)C1)OC]

mixing fresh or dry *Aegiceras corniculatum* raw material with water,
conducting an enzyme extraction using a biological enzyme selected from the group consisting of a pectinase, a cellulase, a neutral protease, and a papain,
filtering and concentrating an extract to a relative density of 1.05-1.1 g/mL at 80-85° C., and
drying to obtain the compound of Formula I.

2. The method according to claim 1, wherein the *Aegiceras corniculatum* raw material consists of above ground parts or below ground parts, wherein the above ground parts are leaves, flowers, stems, or seeds; and the below ground parts are roots.

3. The method according to claim 1, wherein the method comprises the following steps:
   (1) drying and pulverizing the *Aegiceras corniculatum* raw material and sieving;
   (2) mixing the raw material in step (1) with water at a weight ratio of 1:10-1:15, adding 0.2 wt %-0.3 wt % of the biological enzyme based on the weight of the raw material, adjusting pH to 2-10, and stirring at a constant temperature of 35-40° C. for 2-3 h;
   (3) after completing extraction, boiling extracting solution from step (2) for 5-10 minutes and cooling;
   (4) concentrating the extracting solution from step (3) to a relative density of 1.05 to 1.1 g/mL at 80 to 85° C., and drying;
   (5) recrystallizing extracted product from step (4) with ethanol:petroleum ether=3:1 to obtain a light yellow flaky crystal, the compound of Formula I.

4. The method according to claim 3, wherein the drying in step (4) is vacuum drying or spray drying.

5. The method according to claim 1, further comprising:
applying the compound of Formula I to block plants from absorbing heavy metals, and the plants are preferably food crops.

* * * * *